United States Patent [19]
Powell
[11] 3,962,225
[45] June 8, 1976

[54] NITRO(TETRAHYDRO-2H-1,3-THIAZIN-2-YLIDENE)METHYL ALDEHYDES AND KETONES

[75] Inventor: James E. Powell, Modesto, Calif.
[73] Assignee: Shell Oil Company, Houston, Tex.

[22] Filed: Feb. 6, 1975
[21] Appl. No.: 547,417

Related U.S. Application Data

[63] Continuation-in-part of Ser. No. 468,122, May 8, 1974, abandoned.

[52] U.S. Cl. .............................. 260/243 R; 424/246
[51] Int. Cl.$^2$ .............................. C07D 279/06
[58] Field of Search .............................. 260/243 R

[56] References Cited

OTHER PUBLICATIONS

Hirai et al., Chem. Pharm. Bull., vol. 20, pp. 97–101 (1972).

*Primary Examiner*—John M. Ford

[57] ABSTRACT

Novel insecticidal nitro(tetrahydro-2H-1,3-thiazin-2-ylidene)methyl aldehydes and ketones.

3 Claims, No Drawings

NITRO(TETRAHYDRO-2H-1,3-THIAZIN-2-YLIDENE)METHYL ALDEHYDES AND KETONES

This application is a continuation-in-part of copending application Ser. No. 468,122, filed May 8, 1974, now abandoned.

DESCRIPTION OF THE INVENTION

It has been found that useful insecticidal activity is possessed by certain nitro(tetrahydro-2H-1,3-thiazin-2-ylidene)methyl aldehydes and ketones. These aldehydes and ketones are resonance hybrids, the principal forms contributing thereto being described by the formulae:

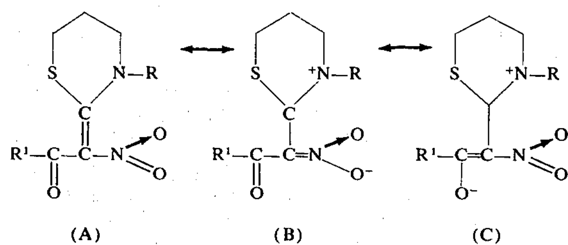

wherein the symbols have the respective meanings set out hereinafter.

The left hand form of the resonance hybrid (Form A) can be designated as a nitro(tetrahydro-2H-1,3-thiazin-2-ylidene)methyl aldehyde or ketone. The central form (Form B) can be designated as a 2-($R^1$-carbonyl-aci-nitromethyl)-5,6-dihydro-4H-1,3-thiazinium hydroxide inner salt. The right-hand form (Form C) can be designated as a 2-(($R^1$-hydroxymethylene)nitromethyl)-5,6-dihydro-4H-1,3-thiazinium hydroxide inner salt.

When R is hydrogen, these compounds may also exist in the corresponding tautomeric enol form which can be described by the formula:

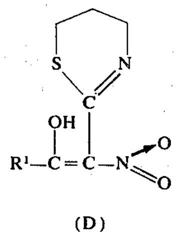

This form (Form D) can be designated as a 2-nitro-2-(5,6-dihydro-2H-1,3-thiazin-2-yl) derivative of the unsaturated alcohol, $CH_2=C(OH)-R^1$.

The resonance hybrid may exist as either of two geometric (cis-trans) isomers, depending upon the spatial relationship of the moieties about the bond between the carbon atom of the nitromethylene moiety and the ring carbon atom to which it is joined.

In this specification, for the sake of simplicity, these compounds will be referred to generally as nitro(tetrahydro-2H-1,3-thiazin-2-ylidene)methyl aldehydes and ketones. This terminology is intended to include all of the contributors to the resonance hybrid, the geometric isomers, and the enol forms, as well as mixtures thereof.

In these compounds, the symbols used in the formulae have the following meanings, respectively:

R is hydrogen, halogen (particularly middle halogen — i.e., chlorine or bromine), or alkyl of from one to eight carbon atoms;

$R^1$ is hydrogen or contains up to thirty carbon atoms and is selected from alkyl, alkenyl, alkynyl, cycloalkyl, cycloalkylalkyl, haloalkyl, haloalkenyl, alkoxyalkyl, alkylthioalkyl, cyanoalkyl, alkylsulfinylalkyl; and aryl, preferably phenyl, optionally substituted on the ring by one or more of halogen, nitro, methylsulfonyl, cyano, alkyl, phenyl, alkoxy, phenoxy; heteroaryl selected from furanyl, 2- and 3-pyridyl; and their corresponding arylmethyl and heteroarylmethyl counterparts.

Desirably, the moiety represented by R contains no more than four carbon atoms, while the moiety represented by $R^1$ contains no more than ten carbon atoms, and when either moiety is aliphatic may be of straight-chain or branched-chain configuration.

The most interesting insecticidal properties appear to be associated with the compounds of the class wherein R is hydrogen or middle halogen, so that these subclasses are preferred.

For illustration, preparation of typical species of the genus is described in the examples included hereinafter. Other typical, illustrative species of this genus of nitro(tetrahydro-2H-1,3-thiazin-2-ylidene)methyl aldehydes and ketones include those wherein the symbols represent the following moieties, this manner of naming the species being accurate yet pointing out the differences between the different species more clearly than if the entire complicated name of each species were to be given:

| | |
|---|---|
| R=H, $R^1$= | chloromethyl |
| | benzyl |
| | 1-naphthylmethyl |
| | 1-propenyl |
| | 2-pyridyl |
| | cyanomethyl |
| | cyclohexylmethyl |
| | ethoxymethyl |
| | perfluoropropyl |
| | ethynyl |
| | 4-methoxyphenyl |
| | 4-methylsulfonylphenyl |
| | 1-naphthyl |
| | cyclopropyl |
| | cyclohexyl |
| | 3-chloroallyl |
| | 3-pyridyl |
| $R^1$—Propyl, R= | methyl |
| | ethyl |
| $R^1$=methyl, R= | methyl |
| | benzyl |
| | 3-chloroallyl |
| | Cl |
| | Br |

Compounds of this invention can be prepared by several general procedures. In some cases, they can be prepared directly as by heating together at a moderately elevated temperature (50°–150°) 5,6-dihydro-2-(methylthio)-4H-1,3-thiazine (A. F. McKay et al., J. Am. Chem. Soc., 80, 8339 (1958)) and the appropriate nitromethyl ketone in the presence of a catalytic amount of zinc ion. This procedure is illustrated in Example 1, hereinafter.

In many cases it will be found that the most facile procedure will be the acylation of the nitromethylene thiazines, which thiazines can be prepared as follows:

Method A: treating a nitroketene dimethyl mercaptole (NKDM) (R. Gompper & H. Schaefer, Berichte, 100, 591 (1967)) with a 3-amino-1-propanethiol (S. D. Turk, et al., J. Organ. Chem., 27, 2846 (1962)), including suitably substituted 3-amino-1-propanethiols, referring to the definitions of R and $R^2$.

Method B: treating 5,6-dihydro-2-(methylthio)-4H-1,3-thiazine (A. F. McKay et al., J. Am. Chem. Soc., 80, 3339 (1958)) with an alkyl nitroacetate (S. Zen, et al., Kogyo Kagaku Zasshi, 74, 70 (1971)) in the presence of a catalytic amount of zinc ion (e.g., zinc chloride) to form the alkyl nitro(tetrahydro-2H-1,3-thiazin-2-ylidene-acetate which is hydrolyzed with a base and decarboxylated by acidification to give the nitromethylene thiazine.

Tetrahydro-2-(nitromethylene)-2H-1,3-thiazines which are R-substituted can be prepared by treating them by either of Methods A or B with a strong alkali metal base in a liquid mixture of tetrahydrofuran and hexamethylphosphoramide or with an alkali metal derivative of the appropriate alcohol in an alcohol as solvent, then treating the resulting intermediate with the appropriate R-sulfate, iodide, bromide, chloride or tosylate.

Method A is carried out by mixing the reactants in a suitable liquid medium such as a lower alkanol. The reaction can in some cases be carried out at essentially room temperature while in other cases gentle to moderate heating (up to 50°C) may be required. Generally, it will be found best to employ a light to moderate excess (5–25%) of the thiol over that theoretically required to react with the mercaptole. Oxygen should be excluded from the reaction zone by conducting the reaction in a nitrogen atmosphere. The product can be recovered by removing the solvent, digesting the residue with water and then extracting the desired product from the aqueous phase by means of a suitable solvent such as methylene chloride.

Method B can be conducted by gradually treating the thiazine with a slight to moderate (5–20%) excess of the nitroacetate ester at a moderately elevated temperature, e.g., 80°–130°C, in the presence of a catalytic amount of zinc ion which conveniently is supplied as zinc chloride to form the thiazine acetate intermediate. While a suitable solvent may be used, in some cases at least, one will not be required. The product can be worked up by conventional extraction and crystallization techniques. The acetate then is decarboxylated by treatment (hydrolysis) with excess base, followed by neutralization of the mixture and recovery of the product. The hydrolysis can be effected at room temperature or at slight to moderate elevated temperatures. Product work-up again can be effected by conventional filtration, extraction, crystallization and elution (chromatographic) techniques.

A thiazine may be substituted on the ring nitrogen atom by treating the thiazine with about an equimolar amount of a strong alkali metal base in a suitable liquid reaction medium at room temperature or at a slight to moderately elevated temperature, then treating the resulting mixture with about the theoretical amount of the sulfate, iodide, bromide, chloride or tosylate of the moiety, R, to be substituted on the nitrogen atom of the thiazine ring. This latter treatment preferably is conducted at temperatures below room temperature, for example, at 0°–15°C. The base used may be, for example, sodium, potassium, or lithium hydrides, their hydroxides or lower alkyls or alkoxides. A suitable liquid reaction medium for use with the metal alkyl or hydride thereof is tetrahydrofuran/hexamethylmethylphosphoramide mixture; where an alkoxide is used, it preferably is the tertiary-butoxide and the solvent is tertiary butyl alcohol. In many cases, at least, it will not be necessary to isolate the intermediate product — the crude reaction mixture containing it may be treated with the R-sulfate, -iodide, -bromide or -tosylate.

As has been indicated, most of the reactions are best conducted in a nitrogen atmosphere, and the techniques for recovery and purification of the intermediate and final products from the crude reaction mixtures are conventional and are illustrated in the examples indicated hereinafter.

Acylation of the nitromethylene thiazine is readily accomplished by heating together at a moderately elevated temperature — for example, 60°–150°C — the thiazine and the appropriate acid anhydride, using a solvent if necessary. In some cases, an excess of the anhydride can be used as the solvent. In other cases, another inert solvent can be used — halogenated alkanes such as methylene chloride and 1,2-dichloroethane are suitable. Recovery of the product is readily effected by conventional techniques such as distillation, extraction, filtration, recrystallization, elution and the like, as illustrated in the examples hereinafter.

Compounds of the invention wherein R is halogen can be prepared by treating the unsubstituted precursor (R = H) with about a 10% molar excess of a halogen or a halogenated compound containing positive halogen at about room temperature, employing a halogenated alkane as solvent. Suitable halogenating agents include chlorine, bromine, N-chloro- and N-bromosuccinimide. Recovery of the product is conveniently effected by filtering the mixture, evaporating the solvent and recrystallizing the product. Other conventional techniques such as distillation, extraction, elution and the like can be used as appropriate.

In some cases, the acylation is conveniently effected by treating the appropriate thiazine with a 1-($R^1$-carbonyl)-3-methylimidazolium chloride by the method described by E. Guibe-Jampel, et al., Bull. Soc. Chim. Fr. 1973 (3) (Pt. 2), pp. 1021-7. According to this method, the imidazolium chloride is prepared by treating 1-methylimidazole with the appropriate acid chloride, $R^1$-C(O)-Cl, preferably in a suitable solvent and at a low temperature, for example, about 0°C. A suitable general method for conducting this procedure comprises adding a solution of the acid chloride in tetrahydrofuran or monoglyme slowly (e.g., dropwise) to a cold (e.g., 0°) solution of the N-methylimidazole in the same solvent, stirring the cold mixture for a period of from about 15 minutes to one hour to ensure complete reaction, then adding to that stirred cold mixture a solution of the thiazine, then warming the stirred mixture to a temperature of from about room temperature to the reflux temperature, and stirring the warm mixture for a time to ensure complete reaction.

The desired product can be isolated from the crude reaction mixture and purified by conventional methods, such as filtration, extraction, crystallization and elution (chromatograhy).

The compound wherein R and $R^1$ each is hydrogen can be prepared as demonstrated in Example 21, following. Preparation of compounds wherein R is alkyl and $R^1$ is hydrogen is illustrated in Example 22, following, in which a by-product of the reaction described in Example 21 is treated with an alkyl halide, such as an alkyl iodide, to form a salt, which is treated with dilute aqueous alkali metal (e.g., sodium) hydroxide solution to form the desired product. Treatment of the by-product precursor with the alkyl halide can be effected by adding a stoichiometric excess of the alkyl iodide to a solution of the precursor, acetone being a suitable solvent, at about room temperature. Treatment of the salt with the alkali metal hydroxide is readily effected by treating a solution of the salt in water with an aqueous solution (for example, a 5% solution) of the hydroxide in water. Isolation of the salt is conveniently effected by evaporating the solvent under reduced pressure.

Recovery of the final product can be effected by conventional techniques, for example, by extracting the final reaction mixture with a solvent, then evaporating the solvent under reduced pressure. The product can be purified by recrystallization techniques.

These procedures for preparing compounds of this invention are illustrated in the following examples of the preparation of particular species of such compounds. In all cases, the identity of the product, and of any intermediate employed, was confirmed by elemental analysis and by infrared and nuclear magnetic resonance spectrum analyses.

EXAMPLE 1

2-nitro-1-phenyl-2-(tetrahydro-2H-1,3-thiazin-2-ylidene)ethanone (1)

A mixture of 3.3 g of 2-nitroacetophenone and 2.94 g of 2-(methylthio)-5,6-dihydro-4H-1,3-thiazine was heated to 115° and 100 milligrams of zinc chloride was added. Heating and stirring was continued at 115°–120° for 2.5 hours. After cooling, the mixture was filtered (with the aid of ethyl acetate) through a short column of florosil to give an amber oil. The oil was chromatographed on silica gel using dry-column technique and a 1:1:2 mixture of tetrahydrofuran/ethyl acetate/hexane for development to give 1 as a salmon-colored solid, m.p.: 137°–140°.

EXAMPLE 2

1-nitro-1-(tetrahydro-2H-1,3-thiazin-2-ylidene)-2-propanone (2)

a. Preparation of Ethyl nitro(tetrahydro-2H-1,3-thiazin-2-ylidene)-acetate (2*a*)

To a mixture of 235 g of 5,6-dihydro-2-(methylthio)-4H-1,3-thiazine and 2 g of zinc chloride at approximately 115° in a nitrogen atmosphere, 263 g of ethyl nitroacetate was added dropwise over a 1.5 hour period. The mixture was held at 110°–120° and the nitrogen atmosphere was maintained during the addition. Evolution of methyl mercaptan ceased after 45 minutes further stirring of the heated mixture when 1 g of zinc chloride was added to the stirred mixture at ca. 115°. After 1.25 hours an additional 1 g of zinc chloride was added and stirring of the mixture at ca. 115° was continued for 1.5 hours. The mixture then was poured into a cooled solution of 2/1 ether/isopropyl alcohol mixture. The crystallized product was collected, washed with ether and dried under reduced pressure to leave a tan solid which on recrystallization from methanol gave 2*a* as a pale yellow solid, m.p.: 105°–106°.

b. Preparation of Tetrahydro-2-(nitromethylene)-2H-1,3-thiazine (2*b*)

2.3 g of 2*a* was added to 10 ml of 20% aqueous sodium hydroxide and the mixture was stirred at room temperature for 12 hours. The resulting solution was treated dropwise with 3.5 g of acetic acid. The addition was accompanied by vigorous gas evolution. The resulting mixture was extracted with methylene chloride and the extract was dried (magnesium sulfate) and concentrated under reduced pressure to give 2*b* as a pale yellow solid, m.p.: 76°–78°.

c. Preparation of 2

4.0 g of 2*b* was added in portions to 50 ml of acetic anhydride at 25°. The solution was heated at 95°–105° for 2 hours. Excess acetic anhydride was removed under reduced pressure to leave 5.0 g of a slightly gummy brown solid which was crystallized from ethyl acetate (after treatment with charcoal) to give 2 as a yellow-brown solid, m.p.: 110°–113°.

EXAMPLE 3

1-(4-methylphenyl)-2-nitro-2-(tetrahydro-2H-1,3-thiazin-2-ylidene)ethanone (3)

A mixture of 8.0 grams of 2*b* and 14.0 g of p-toluic anhydride was stirred under nitrogen and heated at 85°–90° for 7 hours. The mixture then was dissolved in 400 ml of methylene chloride and the solution was washed with 150 ml of concentrated ammonium hydroxide, then with 150 ml water, dried and concentrated under reduced pressure to give a dark gummy solid. The solid was chromatographed on florosil using methylene chloride as eluent to give a white solid which was washed with ether and recrystallized from isopropyl alcohol to give 3 as a white solid, m.p.: 141°–143°.

EXAMPLE 4

1-nitro-1-(tetrahydro-2H-1,3-thiazin-2-ylidene)-2-butanone (4)

A mixture of 5.0 g of 2*b* and 25 ml of propionic anhydride was warmed at 90° and stirred under nitrogen for 3 hours. The reaction product was concentrated under high vacuum at 40°–50° to leave a dark, viscous oil. The oil was filtered through a florosil column using methylene chloride as eluent. A solid was obtained; it was triturated with hexane to give 4 as a pale, yellow solid, m.p.: 77.5°–79.5°.

EXAMPLE 5

1-nitro-1-(tetrahydro-2H-1,3-thiazin-2-ylidene)-2-pentanone (5)

A mixture of 5.0 g of 2*b* and 5.5 g of butyric anhydride was stirred under nitrogen at 85°–90° for 5 hours. The resulting dark oil was cooled, diluted with methylene chloride, washed successively with concentrated ammonium hydroxide, water and saturated salt solution, then dried with sodium sulfate and concentrated under reduced pressure to leave a dark oil which was chromatographed on florosil using methylene chloride as eluent to give a solid which was washed with hexane to leave 5 as a yellow solid, m.p.: 54°–58.5°.

EXAMPLE 6

1-(4-chlorophenyl)-2-nitro-2-(tetrahydro-2H-1,3-thiazin-2-ylidene)ethanone (6)

A mixture of 19.2 g of 2*b*, 36.4 g of 4-chlorobenzoic anhydride and 2 g of zinc chloride in 95 ml of chlorobenzene was stirred under nitrogen and heated at 100°–110° for 3.5 hours. The mixture then was diluted with 600 ml of methylene chloride and filtered to remove undissolved 4-chlorobenzoic acid. The filtrate was washed with 250 ml of concentrated ammonium hydroxide, dried with sodium sulfate and concentrated under reduced pressure to give a dark viscous oil. This oil was chromatographed on florosil using chloroform as eluent. The product was recrystallized from isopropyl alcohol and then ether to give 6 as a yellow solid, m.p.: 119°–123°.

EXAMPLES 7 — 11

By the general technique described in Examples 2–5, 1-nitro-1-(tetrahydro-2H-1,3-thiazin-2-ylidene)-2-octanone (7) was prepared as a pale yellow solid, m.p.: 41°–42°, from heptanoic anhydride and 1-nitro-1-(tetrahydro-2H-1,3-thiazin-2-ylidene)-2-heptanone (8) was prepared as a yellow solid, m.p.: 46°–49°, from hexanoic anhydride, 3-methyl-1-nitro-1-(tetrahydro-2H-1,3-thiazin-2-ylidene)-2-butanone (9) was prepared as a yellow solid, m.p.: 45°–47.5°, from isobutyric anhydride; 1-nitro-1-(tetrahydro-2H-1,3-thiazin-2-ylidene)-2-hexanone (10) was prepared as a dark yellow solid, m.p.: 61.5°–64.0°, from valeric anhydride; 1,1-dichloro-3-nitro-3-(tetrahydro-2H-1,3-thiazin-2-ylidene)-2-propanone (11) was prepared as a yellow solid, m.p.: 123°–124°, from dichloroacetic anhydride;

EXAMPLE 12

1-(3-bromotetrahydro-2H-1,3-thiazin-2-ylidene)-1-nitro-2-propanone (12)

A mixture of 10.1 g of 2 and 10.0 g of N-brompsuccinimide in 150 ml of carbon tetrachloride was stirred at room temperature for 18 hours. The resulting mixture was filtered and the filtrate stripped of solvent under reduced pressure to leave a slightly gummy yellow solid. The solid was treated with ethyl ether and the remaining solid collected (bright yellow solid, m.p.: 101°–104°), then dissolved in methylene chloride. The solution was treated with Norite, filtered and the solvent stripped under reduced pressure to leave a solid which on recrystallization from ethyl acetate gave 12 as a yellow solid, m.p.: 105°–109°.

EXAMPLES 13–16

In a similar manner were prepared:

a. 1-(3-chlorotetrahydro-2H-1,3-thiazin-2-ylidene)-1-nitro-2-propanone (13) as a bright yellow solid, m.p.: 106°–108°.

b. 1-(3-chlorotetrahydro-2H-1,3-thiazin-2-ylidene)-1-nitro-2-pentanone (14) as a yellow solid, m.p.: 47°–50.5°.

c. 1-(3-chlorotetrahydro-2H-1,3-thiazin-2-ylidene)-1-nitro-2-heptanone (15) as an amber liquid, boiling point not determined.

d. 2-(3-bromotetrahydro-2H-1,3-thiazin-2-ylidene)-2-nitro-1-phenyl-ethanone (16), as a yellow solid, m.p.: 119°–119.5°.

EXAMPLE 17

2-nitro-1-(4-nitrophenyl)-2-(tetrahydro-2H-1,3-thiazine-2-ylidene)ethanone (17)

A solution/suspension of 20.4 g of p-nitrobenzyl chloride in 25 ml of monoglyme was added dropwise at 5°–10° to a solution of 9.09 g of N-methylimidazole in 75 ml of monoglyme and the mixture was stirred for an additional 30 minutes at 5°–10°, after which was added dropwise (same temperature) a solution/suspension of 16.0 g of tetrahydro-2-(nitromethylene)-2H-1,3-thiazine in 25 ml of monoglyme, after which the stirred mixture was allowed to warm to room temperature and stirred for 96 hours. The mixture then was taken up in methylene chloride, washed with water and saturated sodium chloride solution, dried ($Na_2SO_4$) and the solvent evaporated under reduced pressure to give an oil which was chromatographed on florosil using methylene chloride as eluent to give a gum, which was washed with ether to give 17, as a yellow solid, m.p.: 158°–160.5°.

EXAMPLES 18–20

In a similar manner, 3-(methylthio)-1-nitro-1-(tetrahydro-2H-1,3-thiazin-2-ylidene)-2-propanone (18) was prepared as a yellow solid, m.p.: 117.5°–119°, from methylthioacetyl chloride; 5-(methylthio)-1-nitro-1-(tetrahydro-2H-1,3-thiazin-2-ylidene)-2-pentanone (19) was prepared as a pale yellow solid, m.p.: 49°–49.5°, from 4-methylthiobutyryl chloride; 4-(methylthio)-1-nitro-1-(tetrahydro-2H-1,3-thiazin-2-ylidene)-2-butanone (20) was prepared as a yellow solid, m.p.: 42°–43° from 3-methylthiopropionyl chloride.

EXAMPLE 21 nitro(tetrahydro-2H-1,3-thiazin-2-ylidene)-acetaldehyde (21)

5.95 g of N,N-dimethyl formamide dimethyl acetal in 25 ml of chloroform was added dropwise at room temperature to a mixture of 8.0 g of 2 *b* in 50 ml of chloroform and the mixture was stirred for one hour at room temperature, then was heated to reflux and stirred for 12.5 hours. The solvent then was evaporated under reduced pressure to give a mushy solid, which was passed through fluorosil, using methylene chloride, then methanol, as eluents. The resulting material then was passed through fluorosil using a 99:1 mixture of methylene chloride and methanol as eluent to give 21 as a yellow solid, m.p.: 171°–172°.

EXAMPLE 22 nitro(tetrahydro-3-methyl-2H-1,3-thiazin-2-ylidene)acetaldehyde (22)

2 *b* was treated with N,N-dimethyl formamide dimethyl acetal as described in Example 21. The crude reaction mixture was freed of solvent and the residue recrystallized with ethyl acetate/methanol. 10 ml of methyl iodide was added in one portion at room temperature to 3.4 g of the resulting solid in 25 ml of acetone and the mixture stirred over-night. The solvent was evaporated under reduced pressure, the residue was crushed under ether and the solid removed and freed of ether by evaporation. 2.3 g of the resulting solid was treated at room temperature with a stoichiometric excess of a 5% solution of sodium hydroxide in water and the mixture stirred for 1 hour. It then was extracted with methylene chloride, the extracts washed with saturated sodium chloride solution, dried ($Na_2SO_4$) and the solvent evaporated under reduced pressure to give 22, as a yellow solid, decomposing at 200°–202°.

Compounds of this invention exhibit useful insecticidal activity, being of particular interest for control of the larvae "caterpillar" or "worm" forms of insects of the genus *Heliothis*, such as *H. zea* (corn earworm, cotton bollworm, tomato fruitworm), *H. virescens* (tobacco budworm); the genus *Agrotis*, such as *A. ipsilon* (black cutworm); the genus *Trichoplusia*, such as *T. ni* (cabbage looper), and the genus *Spodoptera*, such as *S. littoralis* (Egyptian cotton leafworm). Some are also of interest for controlling aphids, whiteflies and houseflies. In tests that have been conducted they have exhibited low, or no, toxicity to other insects such as the 2-spotted spider mite and mosquito larva. Some act very rapidly, providing "quick knock-down" of insects, in some cases even though the compound is not very toxic to the insects.

Activity of compounds of this invention with respect to insects was determined by using standardized tests to establish the $LC_{50}$ dosage (in milligrams of test compound per 100 milliliters of solvent or liquid carrier required in the solution or suspension of test compound used) to kill 50% of the test insects. The test insects were the housefly, corn earworm, mosquito, pea aphid and 2-spotted spidermite, and in some cases, the black cutworm.

All of compounds 1 through 22 were found to be active with respect to the corn earworm. Compounds 2, 4–10, 12–15, 17 and 18 were found to be active with respect to the housefly. Compounds 2, 4–5, 7–10, 12–15, 21 and 22 were found to be active with respect to the pea aphid. Compounds 2 and 3 were tested and found to be active to the black cutworm.

In the course of these tests it was noted that compounds 4, 5 and 8 acted very quickly on houseflies, compounds 2, 5, 10 and 12–15 acted very quickly upon pea aphids and that compounds 1–6, 8–10, 12–15 and 18 acted very quickly upon corn earworms.

The invention includes within its scope insecticidal compositions comprising an adjuvant — that is, a carrier, optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material which may be inorganic or organic and of synthetic or natural origin, with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for compounds of this invention and liquids in which the toxicant is insoluble or only slightly soluble.

Examples of such solvents and liquid carriers generally are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkyaryl sulfonates such as sodium dodecylbenzene sulfonates; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the filed with further solid carrier to give a composition usually containing ½–10%w of toxicant. Granules may be manufactured by agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These cmpositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosage of toxicants of this invention at the locus to be protected — i.e. the dosage to which the insect contacts — is of the order of 0.001% to 0.5% based on the total weight of the formulation, though under some circumstances the effective concentration will be as little as 0.0001% or as much as 2%, on the same basis.

I claim as my invention:

1. A resonance hybrid in which the three significant forms which contribute thereto are represented by the formulae

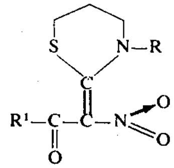

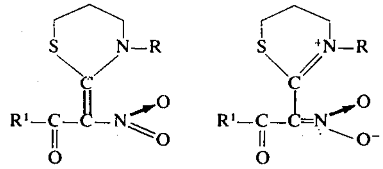

and

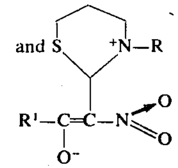

and including when R is hydrogen, the enol form represented by the formula

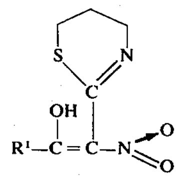

wherein R is hydrogen, halogen or alkyl of from one to eight carbon atoms;

$R^1$ is hydrogen or contains up to 30 carbon atoms and is selected from alkyl, alkenyl, alkynyl, cycloalkyl, cycloalkylalkyl, haloalkyl, haloalkenyl, alkoxyalkyl, alkylthioalkyl, cyanoalkyl, alkylsulfinylalkyl; and phenyl optionally, substituted on the ring by one or more of halogen, nitro, methylsulfonyl, cyano, alkyl, phenyl, alkoxy, phenoxy; heteroaryl selected from furanyl, 2- and 3-pyridyl; and their corresponding phenylmethyl and heteroarylmethyl counterparts.

2. A compound according to claim 1 wherein R is hydrogen, $R^1$ is phenyl.

3. A compound according to claim 1 wherein R is hydrogen, $R^1$ is propyl.

* * * * *